(12) United States Patent
Bjork et al.

(10) Patent No.: US 10,321,944 B2
(45) Date of Patent: Jun. 18, 2019

(54) MIDLINE PARS RETRACTOR

(71) Applicant: Spineology Inc., St. Paul, MN (US)

(72) Inventors: Todd Bjork, Hudson, WI (US); Kyle Wolff, Cottage Grove, MN (US); Shelton Clark, St. Paul, MN (US)

(73) Assignee: Spineology Inc., St. Paul, MN (US)

( * ) Notice: Subject to any disclaimer, the term of this patent is extended or adjusted under 35 U.S.C. 154(b) by 783 days.

(21) Appl. No.: 14/615,140

(22) Filed: Feb. 5, 2015

(65) Prior Publication Data

US 2015/0216517 A1 Aug. 6, 2015

Related U.S. Application Data

(60) Provisional application No. 61/936,199, filed on Feb. 5, 2014, provisional application No. 61/985,911, filed on Apr. 29, 2014.

(51) Int. Cl.
*A61B 17/86* (2006.01)
*A61B 17/02* (2006.01)

(52) U.S. Cl.
CPC .......... *A61B 17/86* (2013.01); *A61B 17/0206* (2013.01)

(58) Field of Classification Search
CPC combination set(s) only.
See application file for complete search history.

(56) References Cited

U.S. PATENT DOCUMENTS

2005/0113645 A1* 5/2005 Sharratt ............ A61B 17/0206
600/227

* cited by examiner

*Primary Examiner* — Sameh R Boles
(74) *Attorney, Agent, or Firm* — Skaar Ulbrich Macari, P.A.

(57) ABSTRACT

A midline retractor provides access for the placement of PARS screws and other surgical sites. A lower profile allows for better visualization of the patients anatomy and provides better access for surgical instruments. The retractor may include integrated lighting, such as fiber optic lighting or other suitable lighting. The blades of the retractor may include a textured profile, such as diamond plating, grooves, etching or any other desired textured treatment on the blades. The texture on the blades may keep tissue from migrating down the blades and may prevent the blades from slipping up and out of the patient. The PARS retractor may include a blade rotation locking mechanism and/or a blade toe feature that allows for ease of use and an adjustable blade toe. The retractor may also include a rack release that provides for free movement of the rack.

15 Claims, 6 Drawing Sheets

MIDLINE PARS RETRACTOR

PRIORITY

This application claims the benefit of U.S. Provisional Application Ser. No. 61/936,199, filed on Feb. 5, 2014 and the benefit of U.S. Provisional Application Ser. No. 61/985,911, filed on Apr. 29, 2014, both of which are hereby incorporated herein by reference in their entirety.

FIELD

The present invention generally relates to retractors. More particularly, the present invention relates to a retractor useful for creating a minimally invasive access opening to an intervertebral space.

BACKGROUND

A variety of tools are available for surgeons for retracting tissue to create a surgical access. However there is a continuing need to provide improved tools for the same, especially system, tools and techniques for creating a minimally invasive access path to an intervertebral space.

SUMMARY

A retractor can be configured as a midline retractor that provides access for the placement of PARS screws. It is contemplated that the retractor can also be used to provide access to other surgical sites.

In certain embodiments, the retractor allows for a small incision and is lower profile than conventional retractors. A lower profile allows for better visualization of the patients anatomy and provides better access for surgical instruments.

In certain embodiments, the retractor may include integrated lighting, such as fiber optic lighting or other suitable lighting.

In certain embodiments, the blades of the retractor may include a textured profile, such as diamond plating, grooves, etching or any other desired textured treatment on the blades. The texture on the blades may keep tissue from migrating down the blades and may prevent the blades from slipping up and out of the patient.

In certain embodiments, the PARS retractor includes a unique blade rotation locking mechanism.

In certain embodiments, a blade toe feature can be provided, which allows for ease of use and an adjustable blade toe.

In certain embodiments, the retractor can include a rack release that provides for free movement of the rack.

The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

Figure 1:
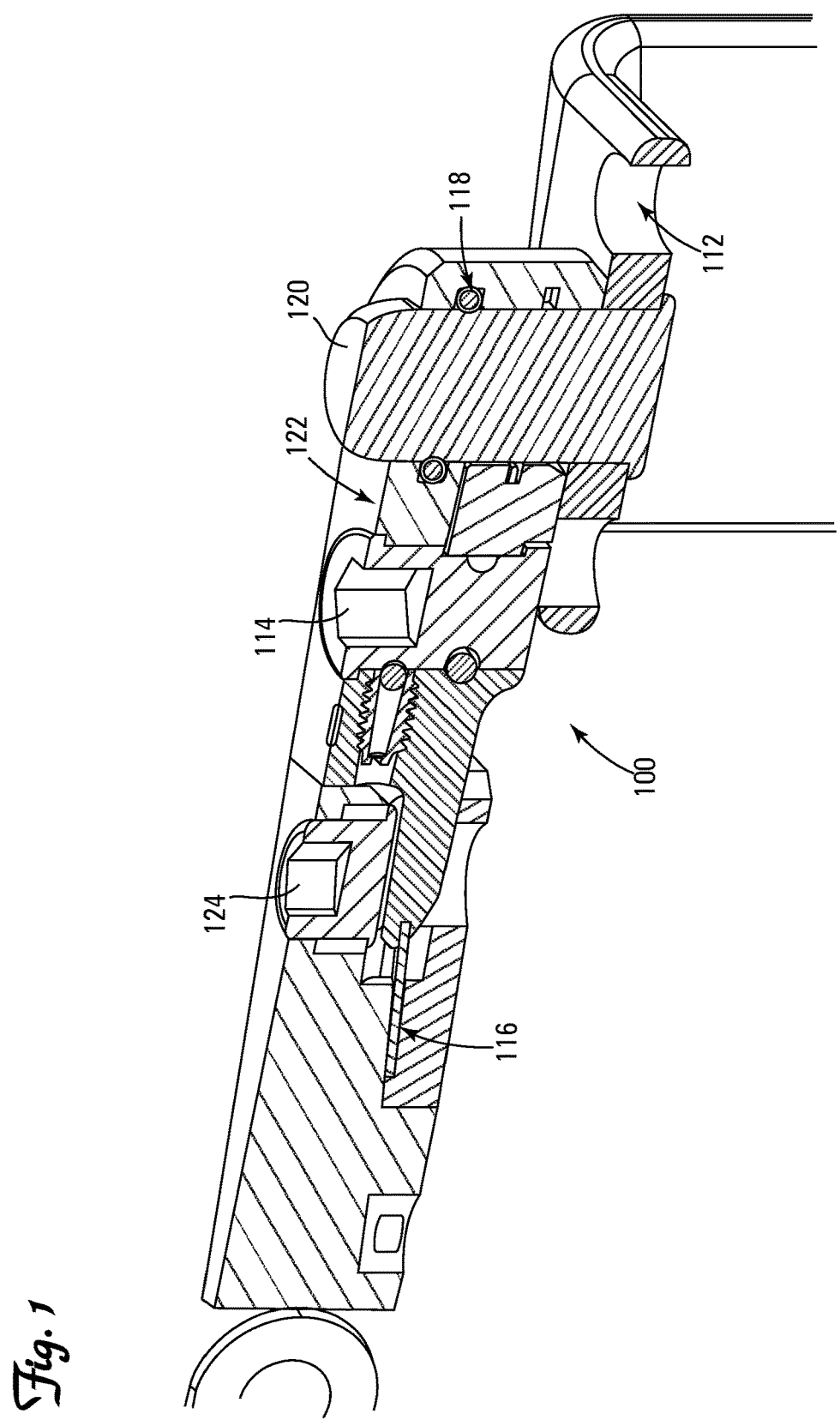
FIG. 1 depicts a view of an embodiment of the present invention.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the spirit and scope of the invention as defined by the appended claims.

DETAILED DESCRIPTION

In the following descriptions, the present invention will be explained with reference to example embodiments thereof. However, these embodiments are not intended to limit the present invention to any specific example, embodiment, environment, applications or particular implementations described in these embodiments. Therefore, description of these embodiments is only for purpose of illustration rather than to limit the present invention. It should be appreciated that, in the following embodiments and the attached drawings, elements unrelated to the present invention are omitted from depiction; and dimensional relationships among individual elements in the attached drawings are illustrated only for ease of understanding, but not to limit the actual scale.

The invention in certain embodiments includes a low profile retractor 100. Retractor 100 may include at least one blade 112. Blade 112 may include a proximal end and a distal end. Blade 112 may rotate between an open position and a closed position relative to the surgical site and any variable position there between.

The retractor of the present invention may include a blade rotation lock mechanism. The blade rotation lock mechanism may allow the user to lock blade rotation. In one aspect, the blade rotation lock mechanism may include a hex key. The hex key may be inserted into a cam hex 114 and then the hex key may be rotated one direction, such as for example, clockwise to lock and another direction, such as for example, counterclockwise, to unlock the blade rotation. Of course, the lock/unlock directions could also be configured to work in reverse.

The retractor may further include a blade toe feature. The blade toe feature allows the blade to be toed out to up to about 15 degrees. In one embodiment, the initial blade toe may be at zero degrees. A spring loaded mechanism 116 may allow for adjustable blade toe angulation and manipulation. A second spring loaded mechanism 118 within a blade nipple 120 provides easy blade attachment to a toe arm 122. In another embodiment, a hex key may be inserted into a tow screw 124 and rotated, creating an adjustable toe out for each blade between the range of about 0 to 15 degrees, creating a total toe out in the range of about 30 degrees between the blades.

Figure 2:
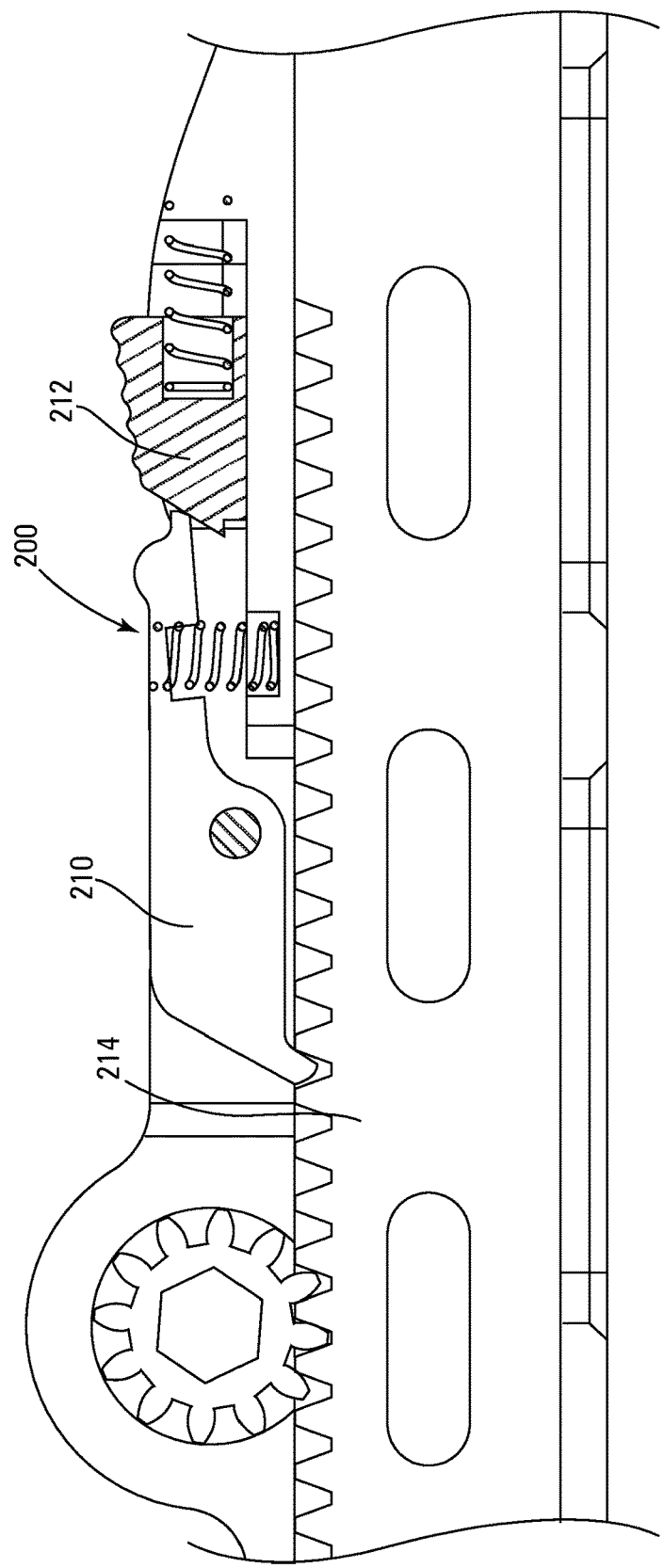
FIG. 2 depicts a view of an embodiment of the present invention.

In yet another example embodiment, the retractor may include a rack release 200. Rack release 200 may include two buttons: rack clicker 210 and release button 212. According to one embodiment, rack ratchet 210 may be a 2 stage push button. The first stage may free the rack while button or lever 210 is pushed. The second stage may occur when button or lever 210 is pushed down until it is locked into place by release member 212, providing free movement of the rack without requiring the user to hold rack ratchet 210. Once the desired position is reached, release member 212 may be pulled back, allowing rack ratchet 210 to reengage with the rack. Additional features and aspects of the invention are depicted in the appended FIGS. 1-2.

Figure 3:
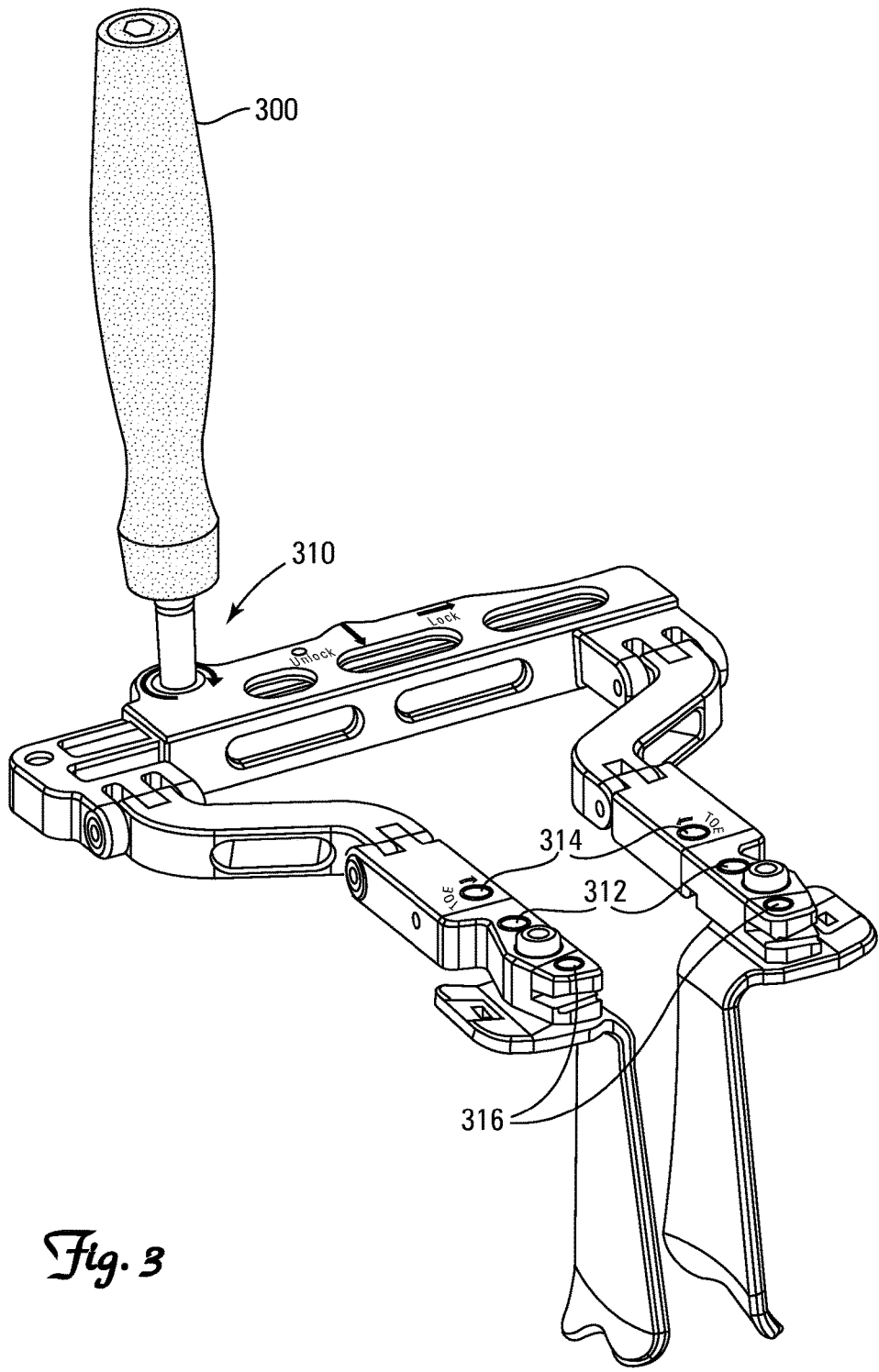
FIG. 3 depicts a view of an embodiment of the present invention.

FIG. 3 depicts an embodiment which may include a universal or hex key 300. Universal key 300 may control many functions of the retractor, unlike conventional retractors which require different keys for each function. Universal key 300 may create retraction with a gear and rack mechanism 310 or other suitable mechanism. Key 300 may also lock rotation of the blades in the retractor frame as shown at 312. Universal key 300 may create toe out of the distal tips of the retractor blades as shown at 314. Key 300 may also lock a light fiber clamp for positional control of the light fiber as shown in 316.

Figure 4:
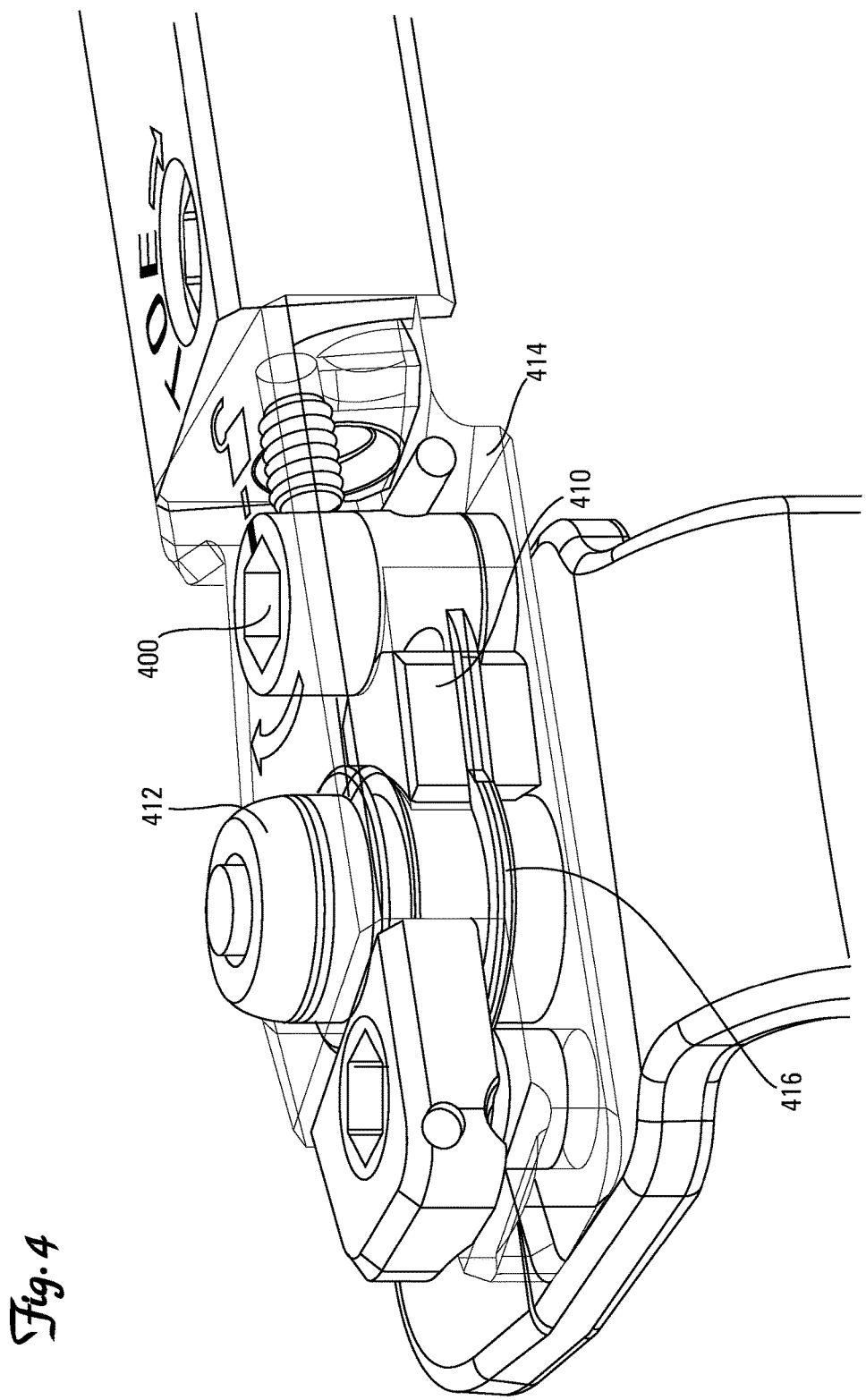
FIG. 4 depicts a view of an embodiment of the present invention.

FIG. 4 depicts an embodiment where universal key 300 may be used. According to one embodiment, key 300 may be placed in cam 400 and then universal key 300 may be rotated clockwise to push cam block 410 against blade nipple 412 to prevent the blade from rotating in the toe arm 414. In another embodiment, cam 400 may be turned counterclockwise to unlock the blade. A spring ring 416 may push cam block 410 away from blade nipple 412 such that the blade may rotate or be removed from toe arm 414.

Figure 5:
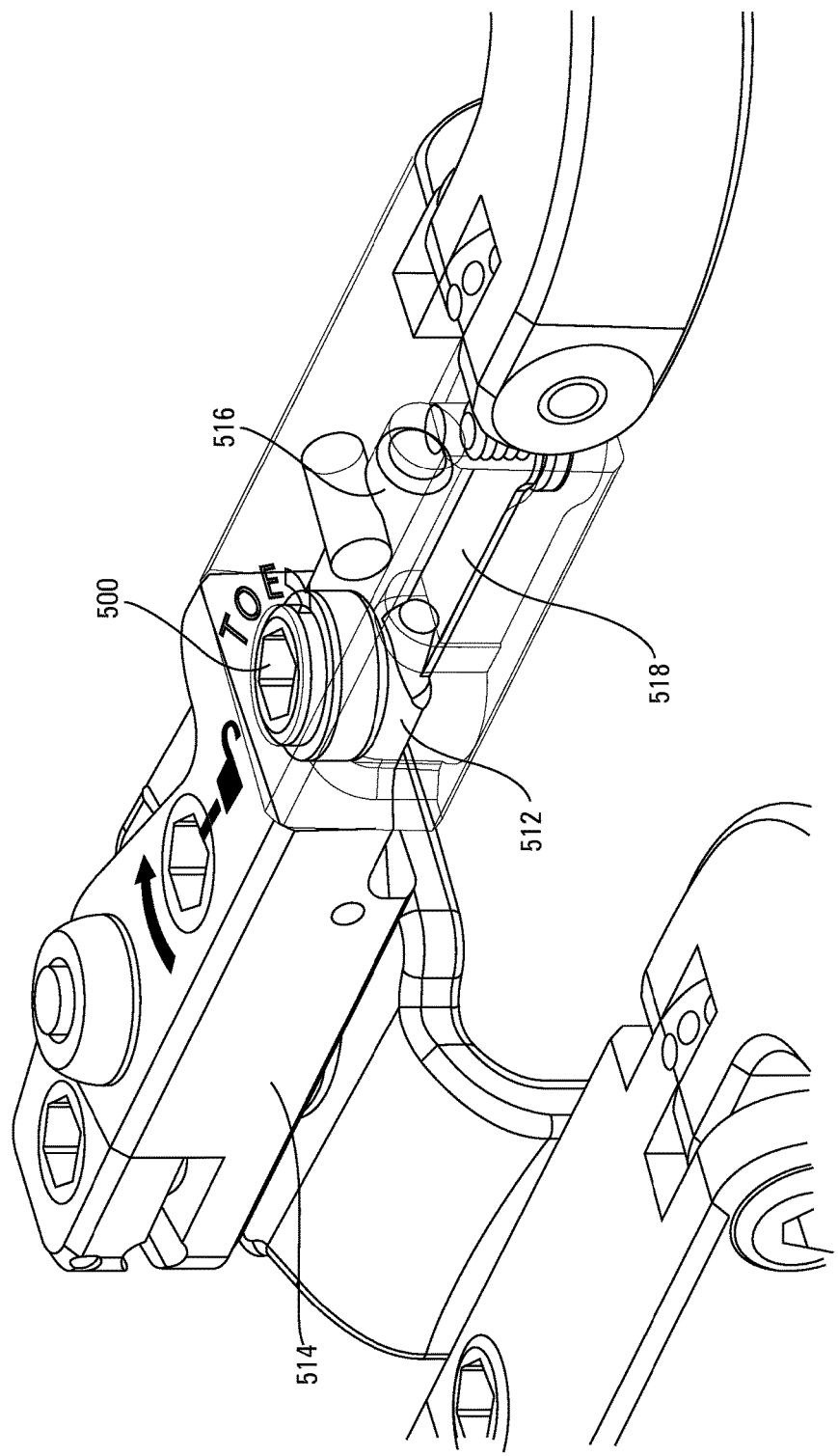
FIG. 5 depicts a view of an embodiment of the present invention.

Referring to FIG. 5, universal key 300 may be placed in toe screw 500. Toe screw 500 may be turned clockwise to create toe of the blade. Screw 500 may be forced against a first shaft 512. Shaft 512 may be connected to body 514. Body 514 may pivot on a second shaft 516. Spring 518 may create force against shaft 512 forcing shaft 512 back up when screw 500 is rotated counterclockwise.

Figure 6:
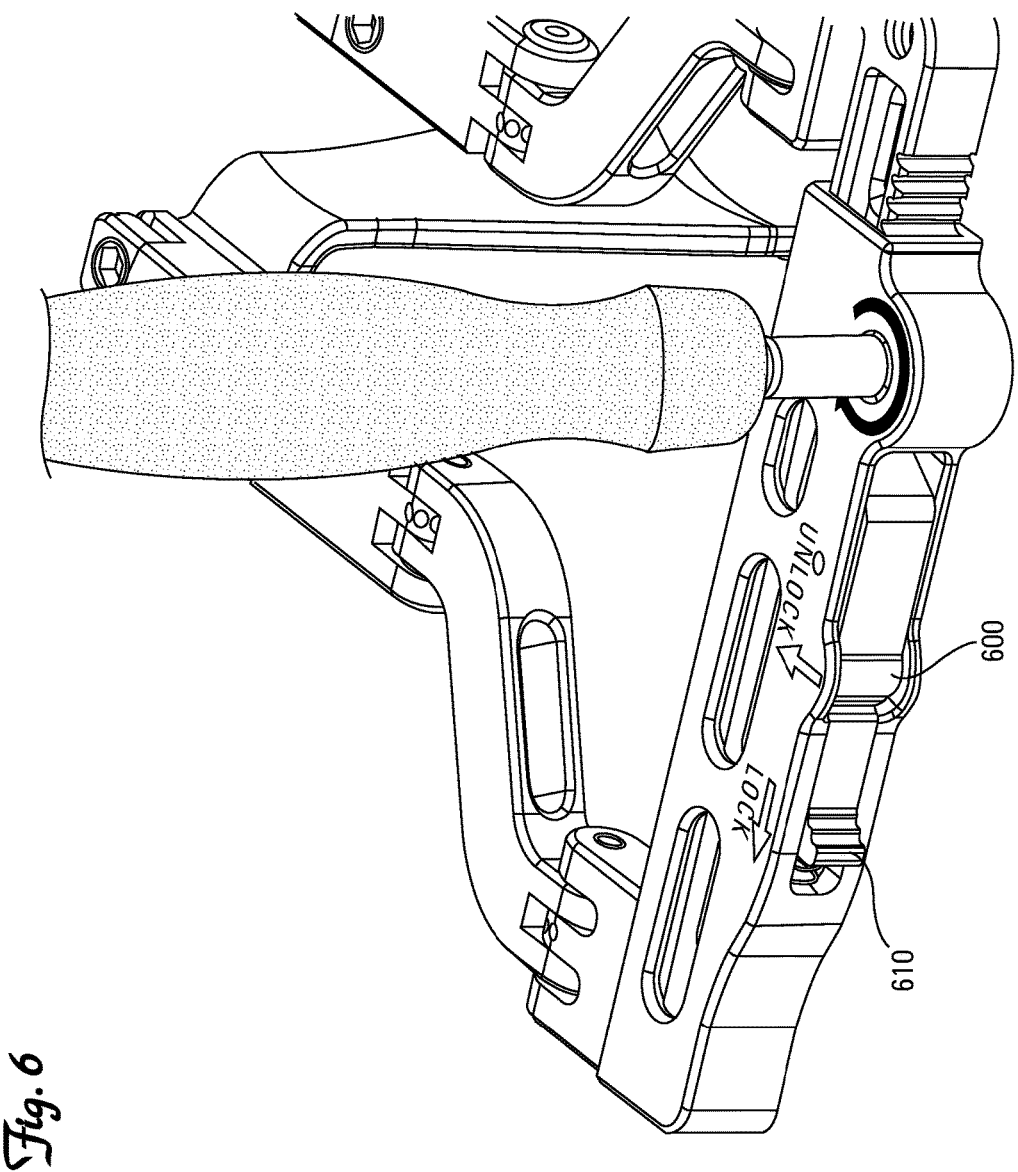
FIG. 6 depicts a view of an embodiment of the present invention.

FIG. 6 depicts another embodiment of the present invention including rack position control buttons 600 and 610 which may include a one-handed dual control mechanism. Button 600 may be pressed to place the rack in a neutral position, allowing for easy alignment of the rack arms onto the blade nipples. Once the blade nipples are connected to the rack arms, rack button 610 may be activated to place the assembly into gear, thus controlling and/or locking the assembly into the open position and preventing the rack from closing under pressure and/or retraction. However, once button 610 is activated, the assembly may still be opened further by turning a universal key. This one-handed dual control mechanism enables the surgeon to adjust the retractor with one hand, thus maintaining a free hand.

The present invention may be embodied in other specific forms without departing from the spirit or essential attributes thereof, and it is, therefore, desired that the present embodiment be considered in all respects as illustrative and not restrictive. Those skilled in the art may recognize other equivalents to the specific embodiment described herein which equivalents are intended to be encompassed by the claims attached hereto.

What is claimed is:

1. A midline retractor for providing access for the placement of PARS screws, the retractor comprising:
    a retractor body;
    a blade coupled to the retractor body, the blade rotatable between an open position and a closed position; and
    a blade rotation lock mechanism provided to the retractor body and coupled to the blade such that a rotational position of the blade can be locked,
    wherein the blade rotation lock mechanism includes a release member to disengage the blade from the blade rotation lock mechanism,
    wherein the blade rotation lock mechanism includes a rack and a ratchet,
    wherein the release member disengages the ratchet from the rack,
    wherein the release member defines two stages,
    wherein the first stage disengages the ratchet from the rack when a force is applied to the release member and reengages the ratchet with the rack when the force is removed from the release member, and
    wherein the second stage disengages the ratchet from the rack when a force is applied to the release member and the ratchet stays disengaged from the rack when the force is removed from the release member.

2. The retractor of claim 1, wherein the release member is a portion of the ratchet.

3. The retractor of claim 1, wherein the ratchet is pivotally mounted such that a rack engagement portion is defined adjacent a first end thereof and an opposing second end thereof defines the release member, and wherein a pivot point for the pivotal mounting is located longitudinally between the engagement portion and the release member.

4. The retractor of claim 1, wherein the blade rotation lock mechanism further includes a reset member that reengages the ratchet with the rack when the reset member is actuated.

5. The retractor of claim 4, wherein the reset member defines a notched portion which captures at least a portion of the release member when the release member is in the second stage.

6. A midline retractor for providing access for the placement of PARS screws, the retractor comprising:
    a retractor body;
    a blade coupled to the retractor body such that a position of the blade can be moved; and
    a blade lock mechanism provided to the retractor body and coupled to the blade such that the position of the blade can be locked,
    wherein the blade lock mechanism includes a release member to disengage the blade from the blade lock mechanism,
    wherein the blade lock mechanism includes a rack and a ratchet,
    wherein the release member disengages the ratchet from the rack when a force is applied to the release member,
    wherein the release member defines two stages,
    wherein the first stage disengages the ratchet from the rack when a force is applied to the release member and reengages the ratchet with the rack when the force is removed from the release member, and
    wherein the second stage disengages the ratchet from the rack when a force is applied to the release member and the ratchet stays disengaged from the rack when the force is removed from the release member.

7. The retractor of claim 6, wherein the release member is a lever portion of the ratchet.

8. The retractor of claim 6, wherein the ratchet is pivotally mounted such that a rack engagement portion is defined adjacent a first end thereof and an opposing second end thereof defines the release member, and wherein a pivot point for the pivotal mounting is located longitudinally between the engagement portion and the release member.

9. The retractor of claim 6, wherein the blade lock mechanism further includes a reset member that reengages the ratchet with the rack when the reset member is actuated.

10. The retractor of claim 9, wherein the reset member defines a notched portion which captures at least a portion of the release member when the release member is in the second stage.

11. The retractor of claim 6, wherein the blade lock mechanism further includes a reset member that reengages the ratchet with the rack when the reset member is actuated.

12. The retractor of claim 6, wherein the ratchet remains disengaged from the rack when the force is removed from the release member.

13. The retractor of claim 12, wherein the blade lock mechanism further includes a reset member that reengages the ratchet with the rack when the reset member is actuated.

14. A midline retractor for providing access for the placement of PARS screws, the retractor comprising:
 a retractor body;
 a blade coupled to the retractor body such that a position of the blade can be moved; and
 a blade lock mechanism provided to the retractor body and coupled to the blade such that the position of the blade can be locked,
 wherein the blade lock mechanism includes means for disengaging the blade from the blade lock mechanism so that the blade is freely movable, and
 wherein the blade lock mechanism further includes means for maintaining disengagement of the blade in the absence of an external force being applied to the means for disengaging the blade from the blade lock mechanism.

15. The retractor of claim 14, further comprising means for resetting the blade lock mechanism so that the position of the blade can be locked.

\* \* \* \* \*